(12) United States Patent
Ashton-Miller et al.

(10) Patent No.: US 6,468,232 B1
(45) Date of Patent: Oct. 22, 2002

(54) METHOD AND APPARATUS FOR MEASURING PROPERTIES OF THE PELVIC FLOOR MUSCLES

(75) Inventors: James A. Ashton-Miller, Ann Arbor, MI (US); John O. L. Delancey, Ann Arbor, MI (US); David N. Warwick, Pinkney, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 27 days.

(21) Appl. No.: 09/615,601

(22) Filed: Jul. 13, 2000

(51) Int. Cl.[7] .................................................. A61B 5/00
(52) U.S. Cl. ..................................... 600/591; 600/593
(58) Field of Search ................................ 600/185, 201, 600/202, 587, 591; 606/191, 197, 198; 33/512

(56) References Cited

U.S. PATENT DOCUMENTS

| | | | |
|---|---|---|---|
| 4,136,681 A | | 1/1979 | Hon |
| 4,216,783 A | | 8/1980 | Kaiser et al. |
| 4,476,880 A | | 10/1984 | Giem et al. |
| 4,543,965 A | | 10/1985 | Pack et al. |
| 4,566,465 A | * | 1/1986 | Arhan et al. ................. 600/591 |
| 4,685,474 A | * | 8/1987 | Kurz et al. ................... 600/591 |
| 4,873,990 A | | 10/1989 | Holmes et al. |
| 4,971,036 A | | 11/1990 | Collins |
| 5,167,237 A | | 12/1992 | Rabin et al. |
| 5,213,112 A | * | 5/1993 | Niwa et al. ................... 600/587 |
| 5,327,908 A | * | 7/1994 | Gerry ........................... 600/587 |
| 5,411,548 A | | 5/1995 | Carman |
| 5,483,832 A | | 1/1996 | Pauser et al. |
| 5,674,238 A | | 10/1997 | Sample et al. |
| 5,785,663 A | * | 7/1998 | Sarvazyan ................... 600/587 |

OTHER PUBLICATIONS

Denise Howard et al., "Racial Differences in the Structure and Function of the Stress Urinary Continence Mechanism," *Obstetrics and Gynecology*, vol. 95, No. 5, pp. 713–717, May 2000.

Carolyn M. Sampselle et al., "Effect of Pelvic Muscle Exercise on Transient Incontinence During Pregnancy and After Birth," *Obstetrics & Gynecology*, vol. 91, No. 3, p. 406–412, Mar. 1998.

D. Howard et al., "Racial Differences in the Continence Mechanism: Function and Structure"; Presentation at the 28th Annual Meeting of Int'l. Continence Society, *Neurourology & Urodynamics*, vol. 17, pp. 418–419, Sep. 1998.

U.M. Peschers et al., "Evaluation of Levator Ani Muscle Strength—Comparison of Four Techniques", Paper#99, Int'l. Continence Society, Jerusalem, Israel, 1998.

(List continued on next page.)

Primary Examiner—Max Hindenburg
(74) Attorney, Agent, or Firm—Fleshner & Kim, LLP

(57) ABSTRACT

An apparatus and method for measuring characteristics of the pelvic floor muscles of a patient includes two or more elongated blades disposed adjacent to one another, one or more sensors that sense an amount of deflection of the first and second blades when the two or more blades are subjected to an external force and a determining unit that determines properties of the pelvic floor muscles in response to an output of the one or more sensors.

84 Claims, 11 Drawing Sheets

OTHER PUBLICATIONS

J.A. Ashton–Miller et al., "An Instrumented Speculum to Measure Levator Ani Muscle Strength: Preliminary Findings", *Journal of the Society for Gynecologic Investigation*, vol. 3, No. 2 (Supplement), Mar./Apr., 1996.

M.C. Dougherty et al., "Variation in Intravaginal Pressure Measurements", *Nurs. Res.*, vol. 40, No. 5, pp. 282–285, Sep./Oct. 1991.

C. Brink et al., "A Digital Test for Pelvic Muscle Strength in Older Women with Urinary Incontinence", *Nurs. Res.*, vol. 38, No. 4, pp. 196–199, Jul./Aug. 1989.

A.M. Worth et al., "Development and Testing of the Circumvaginal Muscles Rating Scale," *Nurs. Res.*, vol. 35, No. 3, pp. 166–168, May/Jun. 1986.

M.C. Dougherty et al., "An Instrument to Access the Dynamic Characteristrics of the Circumvaginal Muscle", *Nurs. Res.*, vol. 35, No. 4, pp. 202–206, Jul./Aug. 1986.

A.M. Shepherd et al., Treatment of Genuine Stress Incontinence with a New Perineometer, *Physiotherapy*, vol. 69, No. 4, p. 113, Apr. 1983.

P.C. Dechow et al., "A Method of Bite Force Measurement in Primates", *J. Biomech.*, vol. 16, No. 10, 4, pp. 797–802, 1983.

* cited by examiner

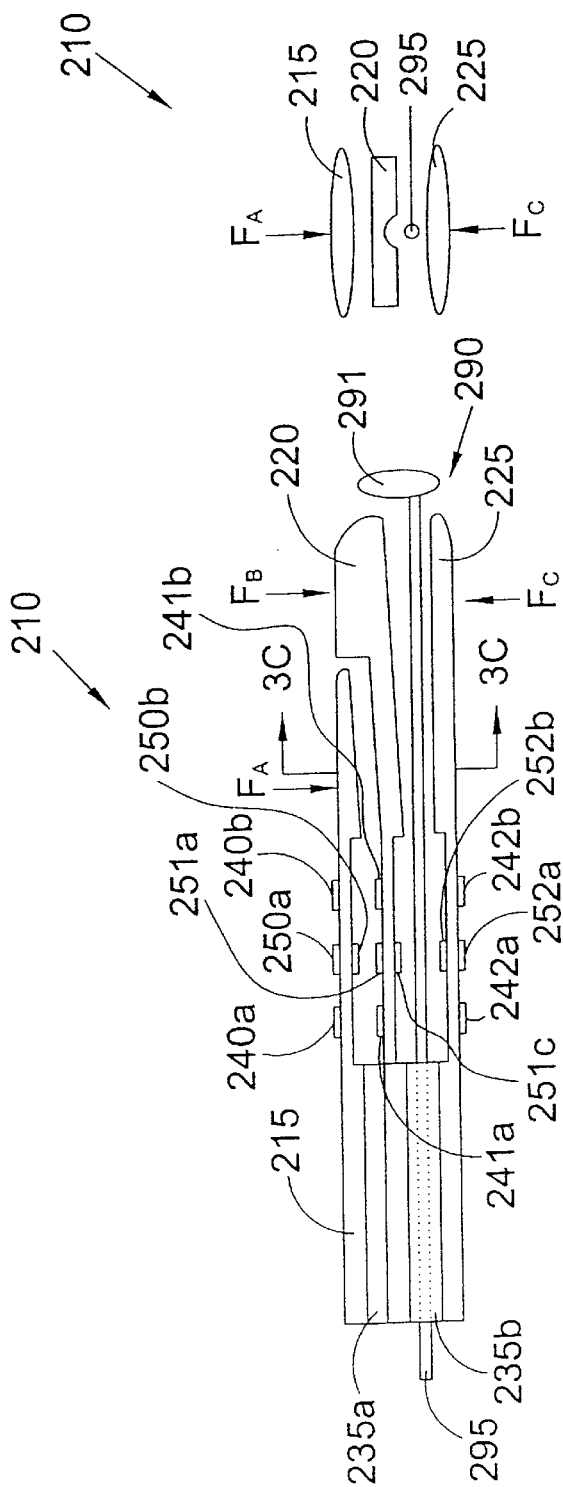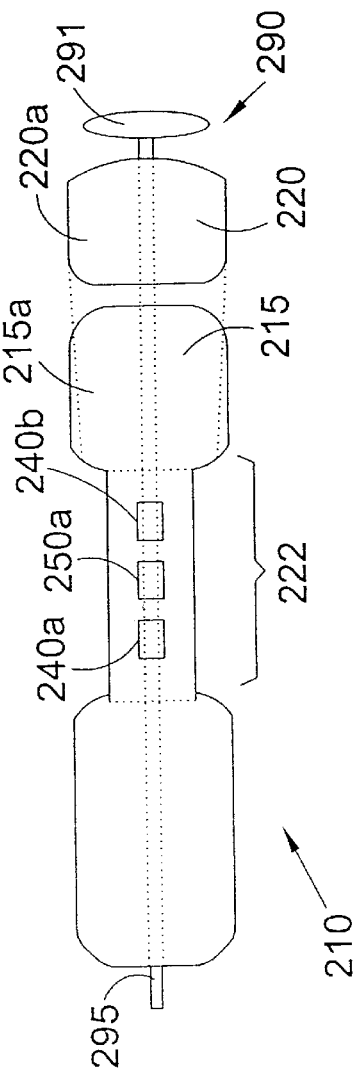
FIG. 3A
FIG. 3B
FIG. 3C

METHOD AND APPARATUS FOR MEASURING PROPERTIES OF THE PELVIC FLOOR MUSCLES

This invention was made with Government support under NIH Grant No. R01 DK 47516. The Government has certain rights in the invention.

BACKGROUND OF THE INVENTION

1. Field of the Invention

A method and apparatus for measuring properties of the pelvic floor muscles. More particularly, a method and apparatus for measuring a strength of the pelvic floor muscles.

2. Background of the Related Art

Approximately one-third of women over the age of 60 years suffer from stress, urinary or fecal incontinence. Approximately one in eleven women or ten (10%) percent suffer from a form of hernia called a prolapse. Pelvic muscle exercises are often prescribed as the first form of conservative treatment for such patients. In the practice of obstetrics, gynecology, urology, physical therapy and nursing, measurement of maximum voluntary pelvic muscle strength is considered a necessary measurement to assess pelvic floor muscle impairment.

Measurement of maximum voluntary pelvic muscle strength is traditionally made by an examiner using one of two methods. In the simplest technique, the examiner subjectively rates the strength of the muscle from the maximum pressure she perceives to be exerted on her two fingers by the levator muscle during a vaginal examination. See, for example, A. M. Worth et al., "Development and Resting of the Circumvaginal Muscles Rating Scale," Nurs. Res. Vol. 35, pp. 166–8, 1986 and C. Brink et al., "A Digital Test for Pelvic Muscle Strength in Older Women With Urinary Incontinence," Nurs. Res., Vol. 38, pp. 196–9, 1989.

In a more advanced technique, measurement of pressure within a balloon device or pressure-making catheter inserted into the vagina or rectum is used to estimate pelvic muscle strength. See, for example, M. C. Dougherty et al., "Development of Testing of an Instrument to Access the Dynamic Characteristics of the Circumvaginal Musculature," Nurs. Res., Vol. 35, pp. 202–206, 1986 and M. C. Dougherty et al., "Variation in Intravaginal Pressure Measurement," Nurs. Res., Vol. 40, pp. 282–5, 1991.

The drawback of the first method is that it is subjective. The drawback of the second method is that it is prone to artefacts including intraabdominal pressure increase, non-isometric test conditions, or passive tissue forces acting on the devices. Neither method measures the contractile force developed by the levator ani under isometric conditions in a known direction.

Indirect measure of pelvic muscle strength is currently made by measuring the myoelectric activity purportedly emanating from the levator ani muscles using surface and intravaginal electrodes or by intravaginal pressure. However, this is not a direct measurement of force developed by the levator ani muscles. Further, the small volume of the levator ani and large volumes of the adjacent thigh muscles make it likely that myoelectric cross-talk from neighboring striated muscles, as well as any muscle fatigue, renders any myoelectric estimates of levator ani "strength" unreliable. See, for example, U. M. Peschers et al., "Evaluation of Levator Ani Muscle Strength-Comparison of Four Techniques," Paper #99, 1998 Int'l Continence Society, Jerusalem, Israel. Likewise, despite its current popularity, for reasons given below, intravaginal pressure is an unreliable method for measuring levator ani strength.

Further, none of the prior art devices allows correction for the mechanical effect of raised intraabdominal pressure (IAP) applied to the measurement device, via tissue-blade contact stresses developed by intraabdominal contents.

The above references are incorporated by reference herein where appropriate for appropriate teachings of additional or alternative details, features and/or technical background.

SUMMARY OF THE INVENTION

An object of the invention is to solve at least the above problems and/or disadvantages and to provide at least the advantages described hereinafter.

A further object of the invention is to provide a method and apparatus capable of providing an objective and accurate quantification of the maximum volitional isometric strength of the pelvic floor muscles in healthy women with temporary neuromuscular damage following childbirth, or other trauma, and women who have fascial detachments of the levator ani. A method and apparatus are provided according to the invention for measuring the maximum isometric voluntary contractile force or strength that can be developed by a patient, the maximum rate of development of that isometric force, and the isometric endurance of the levator ani muscle. That is, pelvic floor muscle contraction force measurements may be made under controlled isometric test conditions. Moreover, the apparatus and method according to the invention may compensate for the effect of changes in intraabdominal pressure on the pelvic floor muscle.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein:

FIG. 3A is a side view of a third embodiment of an apparatus for measuring properties of the pelvic floor muscles according to the invention;

FIG. 3B is a top view of the apparatus of FIG. 3A;

FIG. 3C is a cross-sectional view of the apparatus of FIG. 3A taken along line 3C—3C;

DETAILED DESCRIPTION OF PREFERRED EMBODIMENTS

Figure 1A:
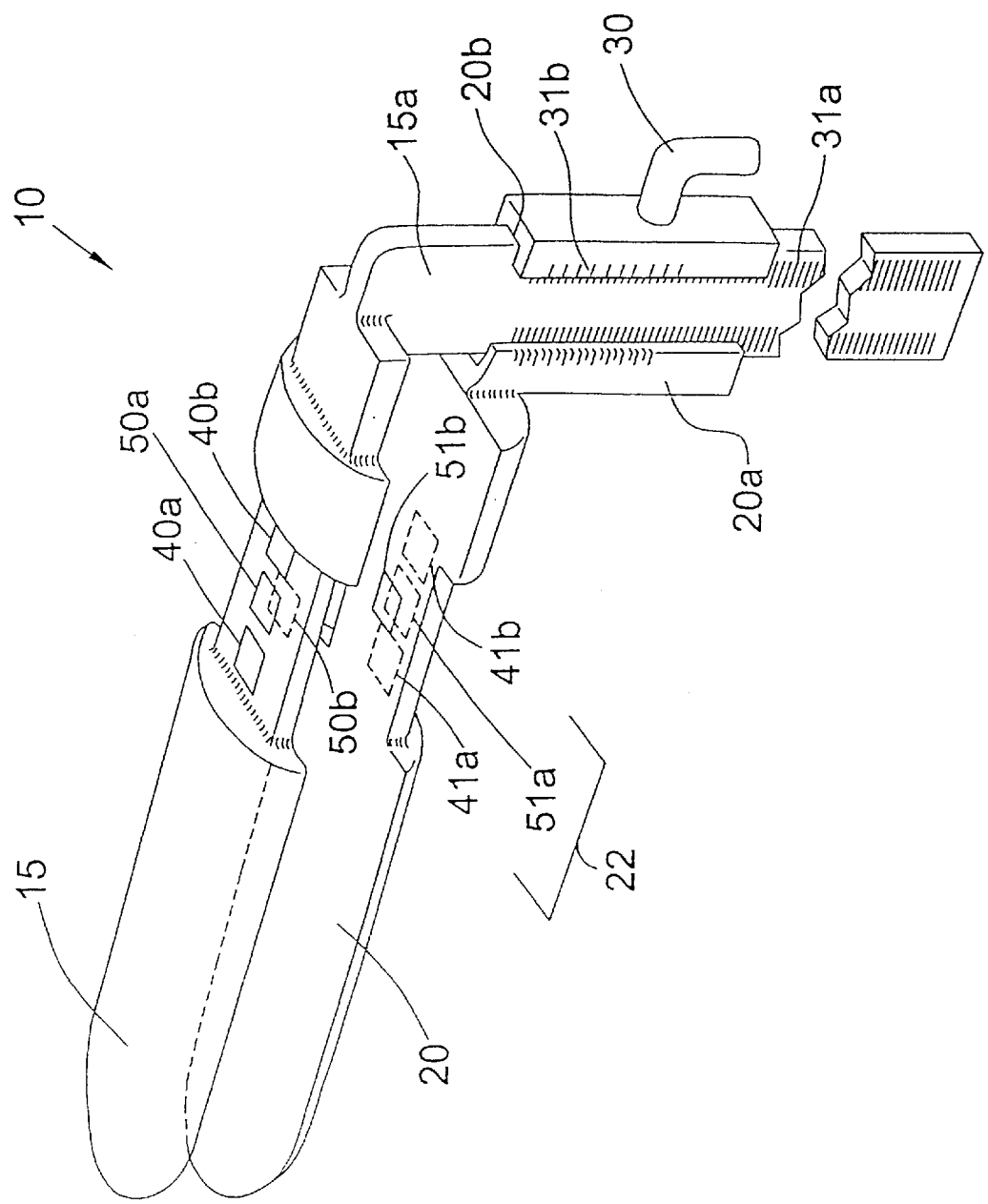
FIG. 1A is a perspective view of a first embodiment of an apparatus for measuring properties of the pelvic floor muscles according to the invention.

A method and apparatus according to the invention were designed for accurately and objectively measuring the contractile force, maximum isometric voluntary strength, the maximum rate of force development and/or the endurance of the levator ani muscle. A traditional gynecological speculum is a two-bladed device that, when closed, resembles the bills of a duck. After being inserted into the vagina, its hinged blades are manually separated by the examiner actively depressing his/her thumb on the blade and moving it to visualize the upper vagina and cervix, and to gain access to the uterus. The apparatus according to the invention differs from the traditional hinged speculum. With the traditional speculum it is not possible to properly control blade separation distance (and hence levator muscle length). Blade separation distance depends upon the interaction between the examiner forcefully attempting to separate the blades with his/her thumb, and the patient attempting to approximate the blades through levator ani contraction.

According to the invention, a plurality of blades is provided disposed adjacent to one another. Preferably, central longitudinal axes of the blades extend substantially in parallel a predetermined distance apart.

According to one embodiment of the invention, the predetermined distance is fixed. For example, a spacer maybe provided which supports the blades at one end and maintains the blades substantially in parallel and a fixed distance apart. The spacer may be formed integral with the blades, or may be a separate piece joined with the blades by some type of fastener.

According to another embodiment of the invention, the predetermined distance is variable and then fixed prior to use. For example, the blades may be provided with mating or interlocking arms that allow the blades to be adjusted with respect to one another and then locked into place prior to use. A graduated scale may be, for example, mounted or engraved on the arms to facilitate adjustment of the arms with respect to one another.

The advantage of having adjustable blade separation distance is that the apparatus may be used to measure the passive or active isometric force developed at any length of the levator ani fibers. For example, the apparatus allows the relationship between isometric force and muscle length to be measured with the muscle in a passive or even anesthetized state, in a maximum active contractile state, or an electrically stimulated state in which stimulus amplitude and frequency are varied.

Further, in a busy clinic, where time is a premium, it is not always convenient or necessary to adjust the blade separation distance for each patient. That is, for certain types of patients it is adequate to standardize a priori the blade separation distance to one of several set distances.

The fixed separation allows testing of the levator ani muscle in an isometric state. In this way, unwanted fluctuations in the levator contractile force due to inadvertent changes in levator muscle length or velocity are eliminated.

The fixed separation, moreover, helps prevent vaginal tissue from becoming trapped between the blades, causing errors in force measurement.

One can estimate the force applied to each blade by measuring its deflection under load using one or more sensors. The sensors may be attached to a display and/or a computer for displaying, processing and/or recording the output therefrom.

The one or more sensors may comprise electrical resistance gages, any practical optical method or device, or piezoelectric or piezoresistive film or devices. Other means may also be appropriate. In the embodiment utilizing electrical resistance gages, each blade may include a narrow waisted gage section machined near its root which is designed to increase the surface strain in that region to values which are easily measurable using standard electrical resistance strain gages.

In one embodiment according to the invention, each of the blades includes a plurality of strain gages. For example, each blade may include three strain gages, two outer gages and one central gage disposed on a respective surface of the blade and a fourth gage disposed on an opposite surface, symmetrically with the central gage. The outer gages of each blade are connected to a standard Wheatstone bridge circuit and the voltage suitably amplified. The output voltage delivered from the strain gages is proportional to the external force (and reaction force) applied to the blades normal to their long axes. A separate Wheatstone bridge circuit incorporating the two center gages of each blade provides a voltage output that is proportional to the moment developed by the force about the root of the blade at that gage location. When, at any instant, that moment is divided by that force, then the position of the applied force along that blade may be calculated at any point in time. The gages and/or Wheatstone bridge circuits may be attached to an amplifier, a display and/or a computer for displaying, processing and/or recording the output therefrom.

In addition, one or more blades may be used to monitor the magnitude and location of the resultant force exerted by intraabdominal pressue (IAP). Information measured from the different signals discussed above can be used to correct the magnitude of the force apparently exerted by the pelvic floor muscles by subtracting the force due to intraabdominal pressure which acts in the same direction.

Most women inadvertently tend to raise IAP when they attempt to contract their pelvic floor muscles. Accordingly, an independent measure of IAP must be made. The apparatus and method according to the invention allow correction for the mechanical effect of raised intraabdominal pressue (IAP) applied to the apparatus, via tissue-blade contact stresses developed by intraabdominal contents. If uncorrected, this elevated IAP will make most devices intended to record pelvic floor muscle strength overestimate that strength.

Thus, when any measure of intraabdominal pressure (whether intravaginal, intrarectal, esophygeal, or other) is measured simultaneously with pelvic floor muscle strength or force using the present apparatus and method, then the effect of this intraabdominal pressure, in terms of the effect of the resulting tissue contact stress from the intraabdominal contents on the transducer blades, may be subtracted from the measured pelvic muscle force.

One way to correct for IAP is to use a manometer or microtip pressure tranducer inserted into the bladder, vagina or rectum to determine the IAP. In the case of the microtip transducer, it can be enclosed in a small balloon containing a fluid, such as water or saline. The IAP can be multiplied by the area of blade upon which it acts and the resulting force value can then be subtracted from the value determined by the apparatus.

Alternatively, IAP may be measured concurrently with pelvic muscle strength utilizing additional blades. The significance of measuring IAP concurrently with pelvic muscle strength is that it enables one to assess how much IAP is being developed while the woman attempts to develop pelvic floor muscle strength. Since devices described in the prior art cannot separate the force developed by the pelvic floor muscles from that developed by IAP, the present devices represent an improvement.

For example, the examiner may estimate an area of the apparatus upon which the IAP acts. This may be achieved by digital palpation of the length of each blade exposed to this pressure. For example, the posterior wall of the vagina may be palpated for the superior edge of the external anal sphincter. More specifically, the cranial extent of the perineal body is identified as being the location where thickening of the connective tissue between the vagina and rectum begins. Since IAP cannot act caudal or anterior to this level (because the rectum is normally closed by sphincteric muscle action), this represents the most caudal margin at which the IAP can act against the posterior blade. Measurement of the distance of this margin from the hymen, or from an external landmark then allows the length of the posterior blade proximal to this margin that is exposed to IAP, to be estimated. Once the exposed blade length is known, then the exposed blade area may be found by multiplying that length by its blade width. Similarly, the anterior wall of the vagina may be palpated to find the location of the inferior margin of the symphysis pubis in the mid-sagittal plane. The IAP will act proximal to this level, hence the length of the anterior blade of the device exposed to IAP can be estimated. The product of this area and the IAP itself allows an estimate of the force acting on each blade due to IAP alone. This force can then be subtracted from the total force that was measured to find the true pelvic floor muscle strength. Alternatively, estimation of these distances can be made from ultrasound or MR images.

Where the one or more sensors comprise a piezoelectric or piezoresistive film or pressure-measuring device, and the anterior surface of the anterior blades and posterior surface of the posterior blades could be covered with multiple, but discrete areas of pressure sensitive film or pressure-measuring devices. The proximal areas would measure IAP while the distal areas would measure the symphyseal pressure or pressure due to pelvic muscle force.

The method and apparatus according to the invention may also include a viscous damping device or an expansion device disposed between two of the plurality of blades. That is, when the blades are unlocked and free to slide toward one another with negligible friction under the action of the external action and reaction forces, and a viscous damping device, such as a piston and cylinder containing an orifice for the contained biocompatible fluid or equivalent device that provides a known force of resistance at a given velocity of shortening, is interposed between the blade roots, then the apparatus may be used to measure the maximum strength of the pelvic floor muscles during a shortening contraction at a given velocity which is measured independently. Similarly, when the blades are unlocked and free to slide away from one another with negligible friction, and an expansion element is interposed between the two blade roots which expands at a known velocity, then the apparatus can be used to measure pelvic floor muscle strength developed under the known rate of muscle fiber lengthening velocity.

The method and apparatus according to the invention may further include one or more tissue blocking devices that prevent tissue ingress between the plurality of blades, which would affect the measurements. The tissue blocking device may be a skirt formed integrally with one or more of the blades, or as a separate piece later joined to the blades. Further, the tissue blocking device may comprises a rod that extends out from between the blades with a tissue blocking element rigidly attached thereto. Other configurations may also be appropriate.

The apparatus according to the invention can be inserted into the vagina or rectum to measure levator ani contraction force when the patient volitionally attempts to contract the pelvic floor muscles. The maximum force developed involuntarily can be measured during a standardized activity such as a cough. For example, when the apparatus is inserted intravaginally in the mid-sagittal plane, the levator ani apply a force to one blade through the posterior vaginal wall, while an equal and opposite reaction force is applied to other blade anterior vaginal wall by compression of soft tissue including the urethra against the inner margin of the symphysis pubis.

The apparatus blades are inserted into the vagina or rectum in the manner of a regular gynecological speculum. In women with a prolapse or damage following vaginal birth, it may be necessary to use a wider blade spacing than normal. To assess the isometric contractile properties of the pelvic floor muscles, including resting tone, maximum isometric levator ani strength, maximum rate of isometric force development, isometric endurance, and rate of relation, the woman is first asked to contract her pelvic floor muscles as hard and as quickly as she can. She may later be asked to hold a similar contraction for as long as she can. The contractile force and moment developed by the levator ani can then be found from the corresponding calibration curves (or regression equation), respectively. The apparatus can be used to measure levator ani contractile forces developed in other maneuvers such as a hard cough, sneeze, or valsalva (straining) maneuvers in both the supine and standing postures.

Following calibration of the input force versus output signal relationship, the apparatus may be used to quantify the active contractile and passive tissue properties of the pelvic floor muscles. These include maximum isometric pelvic muscle strength, rate of developing isometric strength, muscle endurance and fatigue properties at a fixed muscle fiber length, and the contractile force resulting from electrical muscle stimulation intravaginally or intrarectally in women and intrarectally in men.

The method and apparatus according to the invention specifically lend themselves to assessing changes in pelvic floor muscle strength following a Kegel exercise intervention of the type described in C. M. Sampselle et al., "Effect of Pelvic Muscle Exercise on Transient Incontinence During Pregnancy and After Birth", Obstetrics and Gynecology, Vol. 91, No. 3, pp. 406–412, March 1998, which is incorporated herein by reference. Additionally, the apparatus and method can be used as a training or biofeedback device in obtaining pelvic floor muscle strengthening through exercises to give the subject biofeedback or knowledge of results on any of the measured parameters.

A first embodiment of an apparatus for measuring properties of the pelvic floor muscles according to the invention is shown in FIG. 1A. The apparatus 10 of FIG. 1A includes two elongated blades 15, 20. The blades 15, 20 are preferably shaped to facilitate insertion into, for example, the vagina or rectum. The blades 15, 20 are preferably approximately 2.5 cm in width; however, other widths may also be appropriate.

Figure 1B:
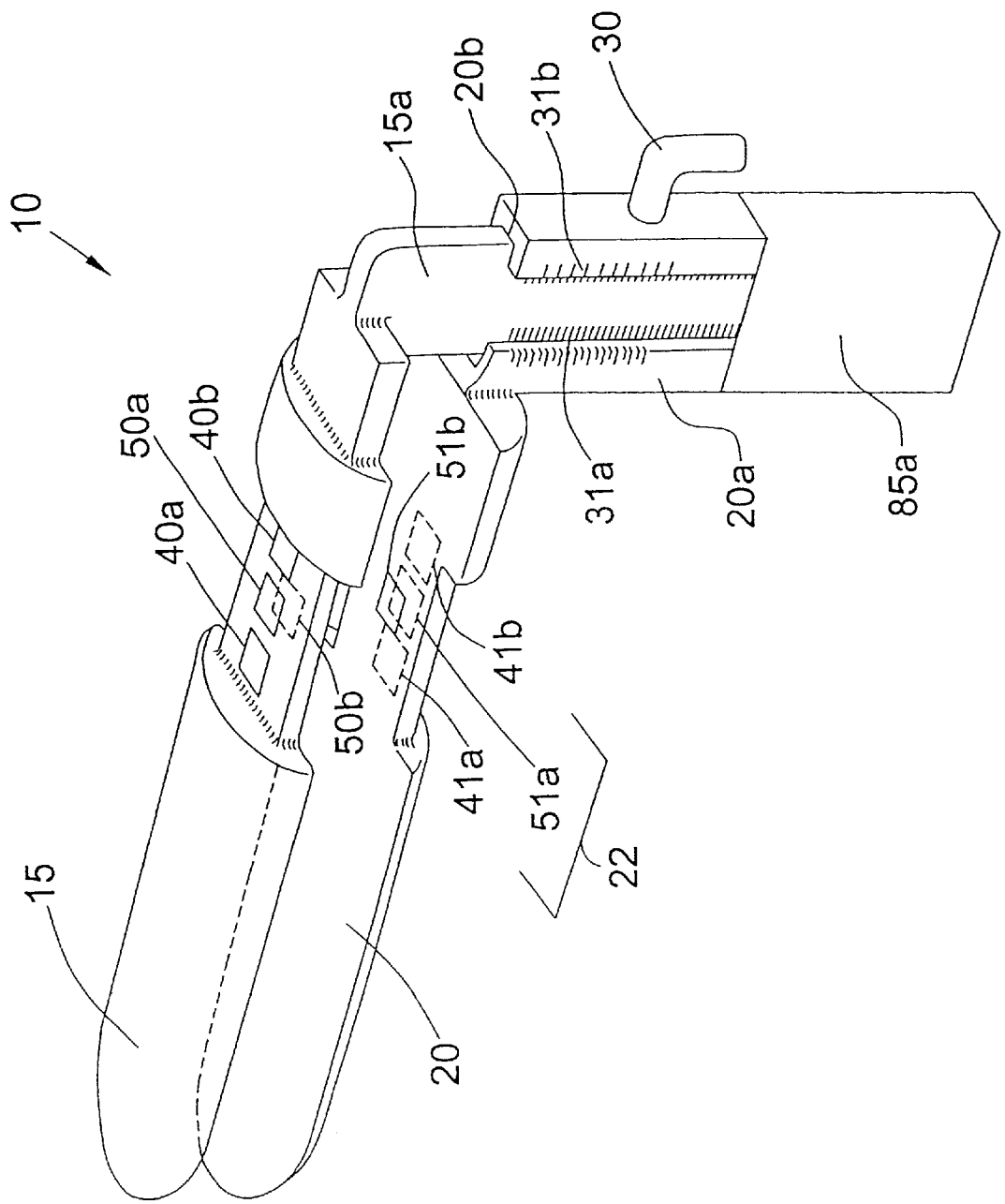
FIG. 1B is a perspective view of an alternative of the apparatus of FIG. 1A.
Figure 1C:
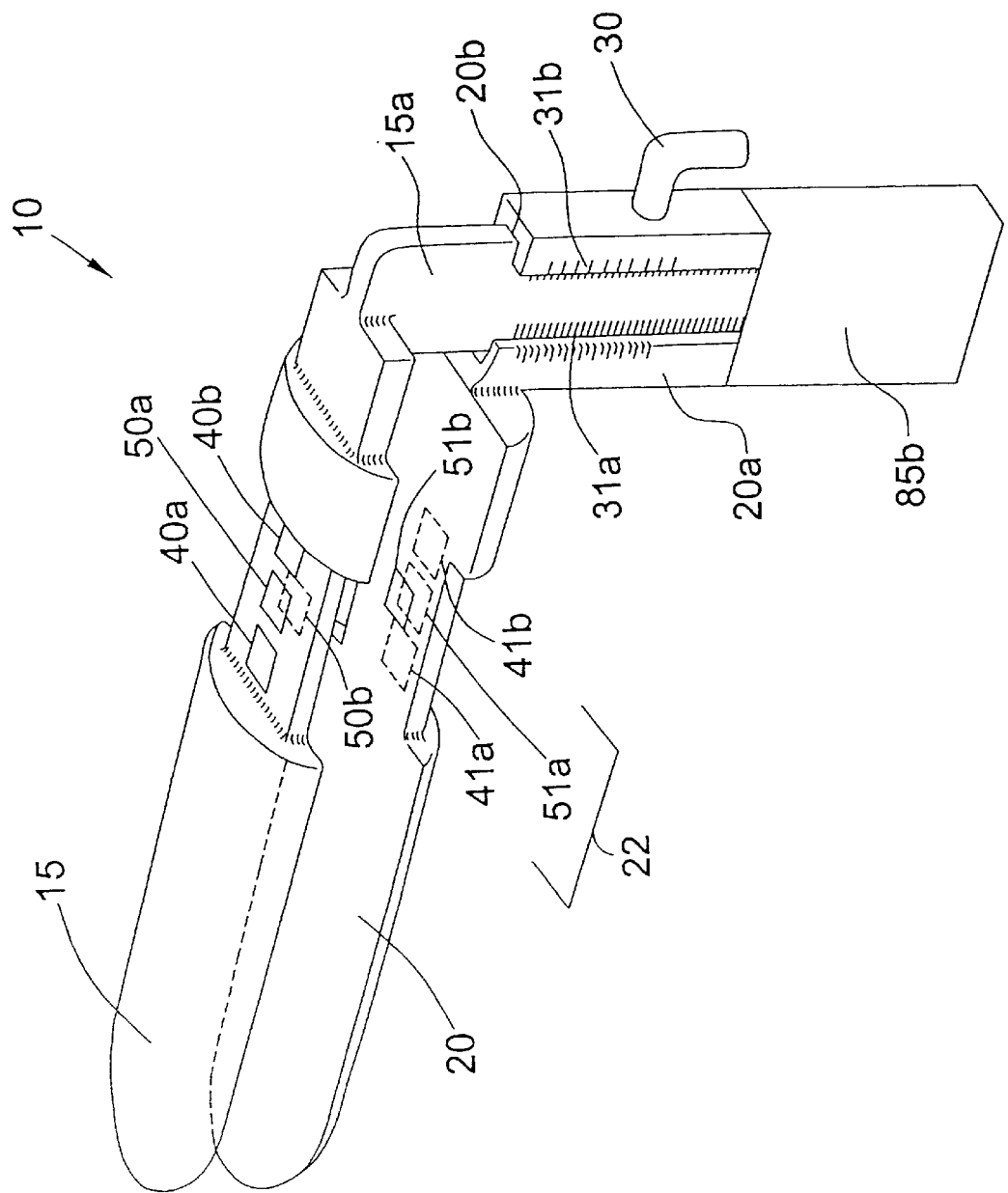
FIG. 1C is a perspective view of another alternative of the apparatus of FIG. 1A.
Figure 1D:
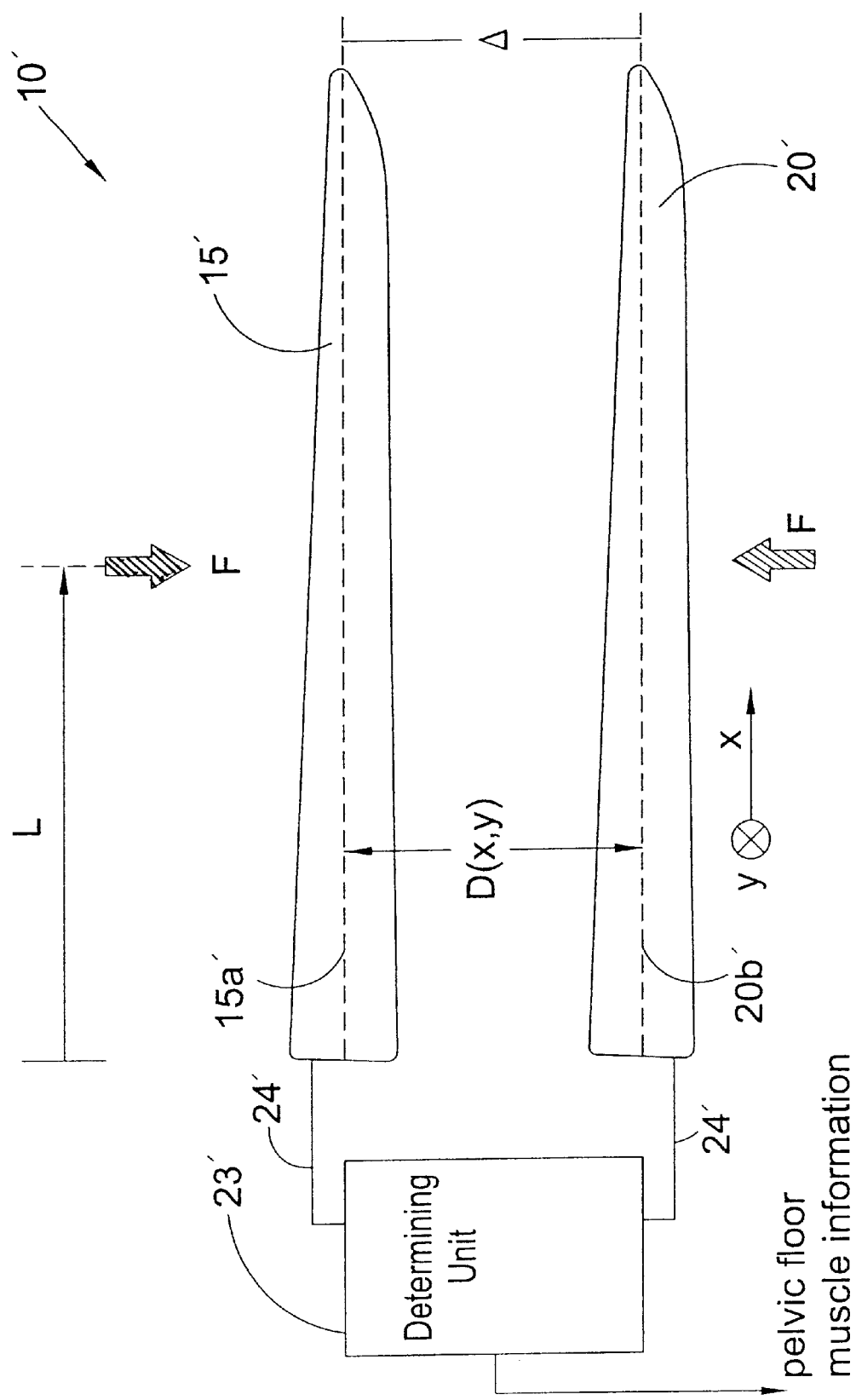
FIG. 1D is a schematic diagram showing the relationship between central longitudinal axes of the blades of an apparatus similar to the apparatus of FIG. 1A.

FIG. 1D shows a more generalized version of an apparatus 10' for measuring properties of the pelvic floor muscles. Extension units 15' and 20' represent a more generalized version of blades 15, 20, respectively. Extension units 15' and 20' each have at least one or more sensors (not shown) interspersed and incorporated therein and/or thereon. Also, extension units 15' and 20' each have a representative surface 15a' and 20b', respectively, which can be defined according to the relative shapes of extension units 15' and 20', respectively. The distance D(x, y) between representative shapes 15a' and 20b' represents the distance between extension units 15' and 20' for all points in an (x, y) plane, where the x axis is depicted along the longitudinal direction of extension units 15' and 20' and the y axis is directed into FIG. 1D. A determining unit 23' is electrically or possibly optically coupled to the sensors via coupling links 24'. The sensors in the extension units 15' and 20' can be any type of strain sensor, and extension units 15' and 20' can be made of any type or mixture of materials sufficient to service motion or strain within extension units 15' and 20'. The sensors can output an optical or electrical signal which contains such strain or motion information via links 24' to determining unit 23'.

The determining unit 23' works in conjunction with the sensors and extension units 15' and 20' in the following manner. Determining unit 23' receives signals from the sensors in extension units 15' and 20' and combines and/or decouples information to yield or determine properties (information) of the pelvic floor muscles. Prior to insertion of apparatus 10' into a subject, representative shapes 15a' and 20b' have a fixed relationship D(x, y) to each other, and accordingly, extension units 15' and 20' have a fixed relationship with respect to each other. After insertion, D(x, y) will have a slightly altered value for points (x, y), depending on the physical makeup and/or physiology of the subject. This is the case even prior to the subject's exerting any pelvic muscle contraction. Determining unit 23' may be adjusted or the values output therefrom may be stored before the subject is asked to contract the pelvic floor muscles.

The number of sensors distributed within or on extension units 15' and 20' must be determined according to the type of pelvic floor muscle information to be output by the determining unit 23'. A minimum of at least one sensor in each extension 15' and 20' is required to provide sensor signals via link 24' to determining unit 23' so that the determining unit 23' can in turn output pelvic floor muscle information.

The determining unit 23' may be circuitry that passively and/or actively decouples the pelvic floor muscle information from sensor signals output from sensors contained in extension units 15' and 20'. The determining unit may also include processing capabilities to process certain information. A processor or computer may be coupled to determining unit 23' or possibly be part of determining unit 23'. Information can be input or processed via such computer or processor in conjunction with sensor signals output from sensors in extension units 15' and 20' or with the pelvic floor muscle information. This information may include certain information regarding the subject such as image information related to the subject's pelvic floor muscle physiology. Other information may include the subject's physical characteristics such as height, weight, etc.

In several embodiments below, it will be shown that two or more sensors are necessary on each extension unit 15' and 20' in order to decouple both force and moment information. The relationship or distance D(x, y) between representative shapes 15a' and 15b' is changed by a change in the distribution of forces and moments on extension units 15' and 20', as well as the type of materials from which the extension units 15' and 20' are constructed.

In one embodiment, extension units 15' and 20' correspond to two blades 15, 20 and are preferably arranged substantially in parallel and spaced a predetermined distance apart. Even here, however, the particular external shape of the respective blades may vary. As shown in FIG. 1D, in equilibrium, the central longitudinal axes of the blades are preferably substantially parallel in which case D(x, y) is fixed over the (x, y) plane and spaced a predetermined distance apart Δ. When the blades are subjected to an external force, the blades deflect changing Δ. This change in Δ allows a variety of measurements to be made by the apparatus.

In the embodiment shown in FIG. 1B, the predetermined distance between the blades may be adjusted. For example, the first blade 15 may include an arm 15a that extends substantially perpendicular to the first blade 15, while the second blade 20 may include an arm 20a that extends substantially perpendicular to the second blade 20. The arm 20a would include a groove 20b that receives and mates with the arm 15a so that the arm 15a is slidably disposed within the arm 20a.

Once adjusted to a desired spacing, the blades are locked with respect to one another using a pin or screw 30, as shown in FIG. 1A, which engages with apertures (not shown) provided in arms 15a, 20a; however, a detent engaging with notches or holes, or other means for locking the arms with respect to each other may also be appropriate.

The spacing between the blades is preferably adjustable from approximately 0 to 10 cm. In this way, the device can accommodate the smaller vaginal hiatus of healthy women, as well as the larger hiatus in those with vaginal vault prolapse. A graduated scale 31a, 31b may be mounted or engraved on the arms 15a, 20a to facilitate adjustment. Other configurations that allow the two blades to be adjusted and fixed with respect to each other are also permissible.

Alternatively, a viscous damping device 85, as shown in FIG. 1B, that provides a predetermined force of resistance at a given velocity may be provided between arms 15a, 20a. Then, the apparatus may be used to measure the maximum strength of the pelvic floor muscles during a shortening contraction of a given peak velocity which is measured independently. Also, an extension device 85b may be provided that expands at a known velocity, as shown in FIG. 1C. Then, the apparatus may be used to measure the pelvic floor muscle strength developed under the known rate of muscle floor lengthening velocity.

The blades 15, 20 and arms 15a, 20a are preferably formed of a structural elastic material, such as anodized aluminum, stainless steel, titanium or a rigid structural material. The modulus of elasticity, cross-sectional geometry and overall geometric design are selected so as to yield sufficient microstrain in each gage section under full load, thereby yielding acceptable resolution of the smallest force that is clinically meaningful.

The first blade 15 includes, preferably within a gage section 22, which may be narrowed, near the root of the blade, a plurality of strain gages 40a, 50a, 40b mounted on an upper surface of the blade and a strain gage 50b mounted on a lower surface of the blade, symmetrically with gage 50b. The second blade 50b includes, preferably within the gage section 22, strain gages 41a, 51a, 41b mounted on an upper surface of the blades, and a strain gage 51b mounted on a lower surface of the blade, symmetrically with strain gage 51a.

The strain gages are separated by a known distance. When the blades are fixed with respect to each other. The strain gages are then utilized to measure deflection of the blades. Alternatively, optical means (not shown) or piezoresistive or piezoelectric means (not shown) may be utilized to measure deflection. A waterproof coating (not shown) may be applied over the gages to seal them from the effects of body fluids, cleaning solvents or sterilizing fluid.

The strain gages of each blade are preferably connected to one or more Wheatstone bridge circuits, an amplifier, a display and/or a computer so that the apparent force and moment developed by the pelvic floor muscles can be determined. The location at which a force acts on the blades may then be calculated.

For example, the outer pairs of the outer gages of each blade may be connected to a Wheatstone bridge circuit and amplifier. With such a configuration, the apparatus delivers an output voltage signal that is proportional to the force and reaction force applied to the blades by the levator ani muscle, whether in a relaxed state or an active contraction, whether voluntary or involuntary, applied at right angles to, and in the plane of, the two blades. The two center gages of each blade may be connected to a similar but separate Wheatstone bridge circuit that yields an output signal that is proportional to the moment, M, developed by the levator ani about that gage location. By dividing the estimated moment by the estimated force, the location, L, at which the resultant levator ani force acts on the blades can be calculated. Using an iterative approach, an improved estimate of the levator force, F, can be found knowing the location at which it is calculated to act on the blades (FIG. 1D).

Figure 5A:
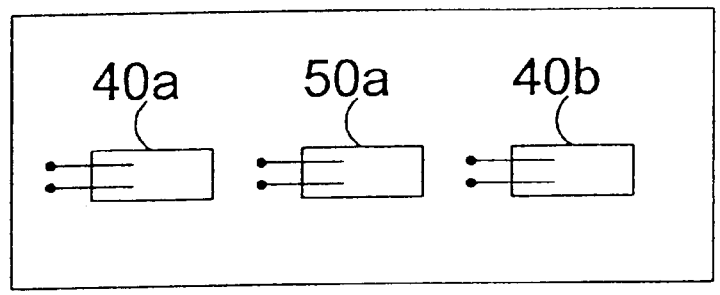
FIGS. 5A–5D are schematic diagrams showing the layout of gages on surfaces of the two blades of the apparatus of FIG. 1A.
Figure 5B:
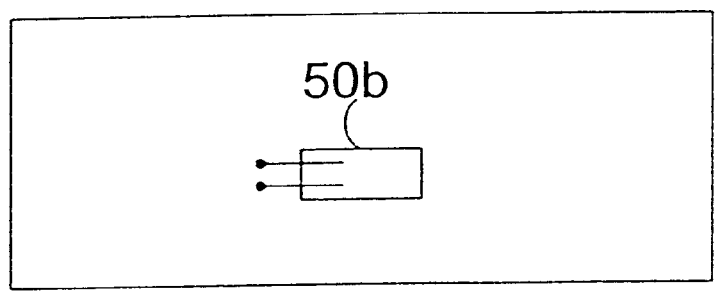
Figure 5C:
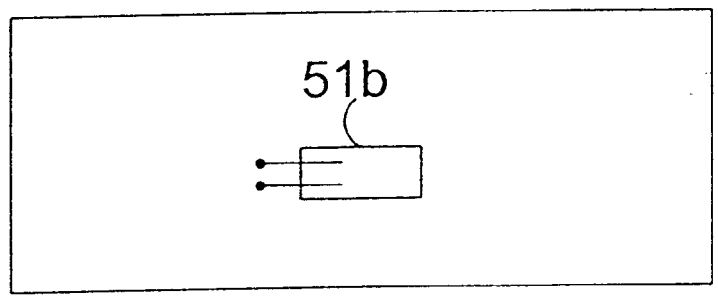
Figure 5D:
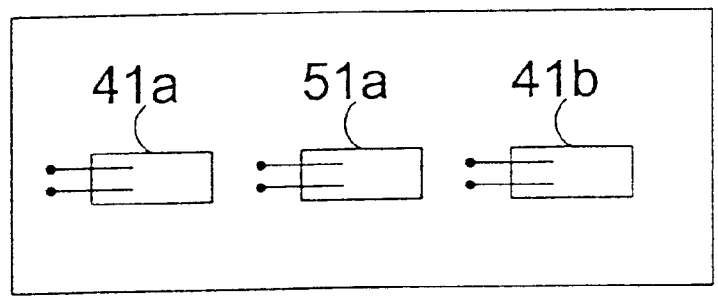
Figure 5E:
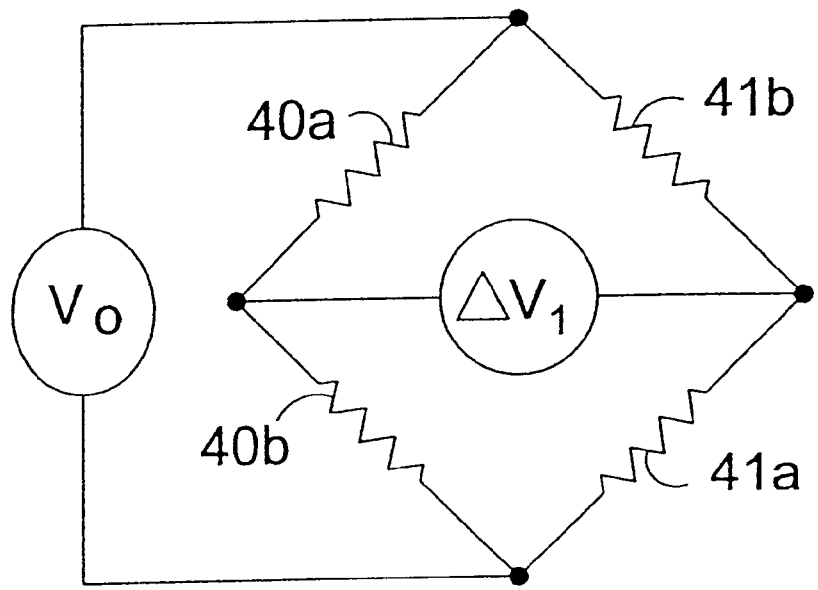
FIGS. 5E–5F are circuit diagrams of Wheatstone bridge circuits of the apparatus of FIG. 1A.
Figure 5F:
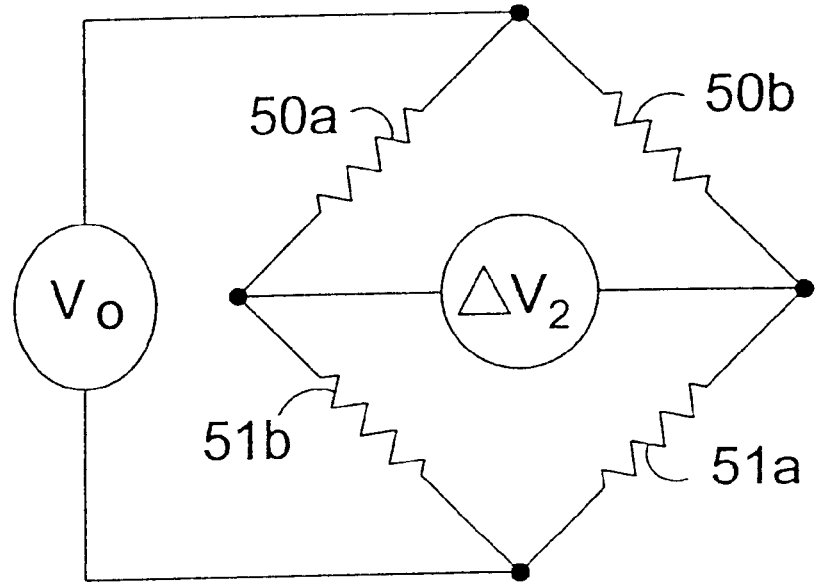

FIGS. 5A–5F show the layout of the gages of the apparatus of FIG. 1A, as well as the wiring layout. In particular, FIG. 5A is a schematic diagram of the gage layout on an upper surface of the first blade 15, and FIG. 5B is a schematic diagram of the gage layout on a lower surface. FIG. 5C is a schematic diagram of the gage layout on the upper surface of the second blade 20, and FIG. 5D is a schematic diagram of the gage layout on the lower surface. FIG. 5E is a circuit diagram of the Wheatstone bridge circuit for the apparatus of FIG. 1A utilized to determine the force acting on the blades. FIG. 5F is a circuit diagram of the Wheatstone bridge circuit for the apparatus of FIG. 1A utilized to determine the moment acting on the blades.

To prevent the transmission of infectious agents from one patient to another, a clean, disposable, condom may be placed over each blade before insertion into the vagina. Further, the speculum blades may be washed, cleaned and sterilized after use.

Figure 2A:
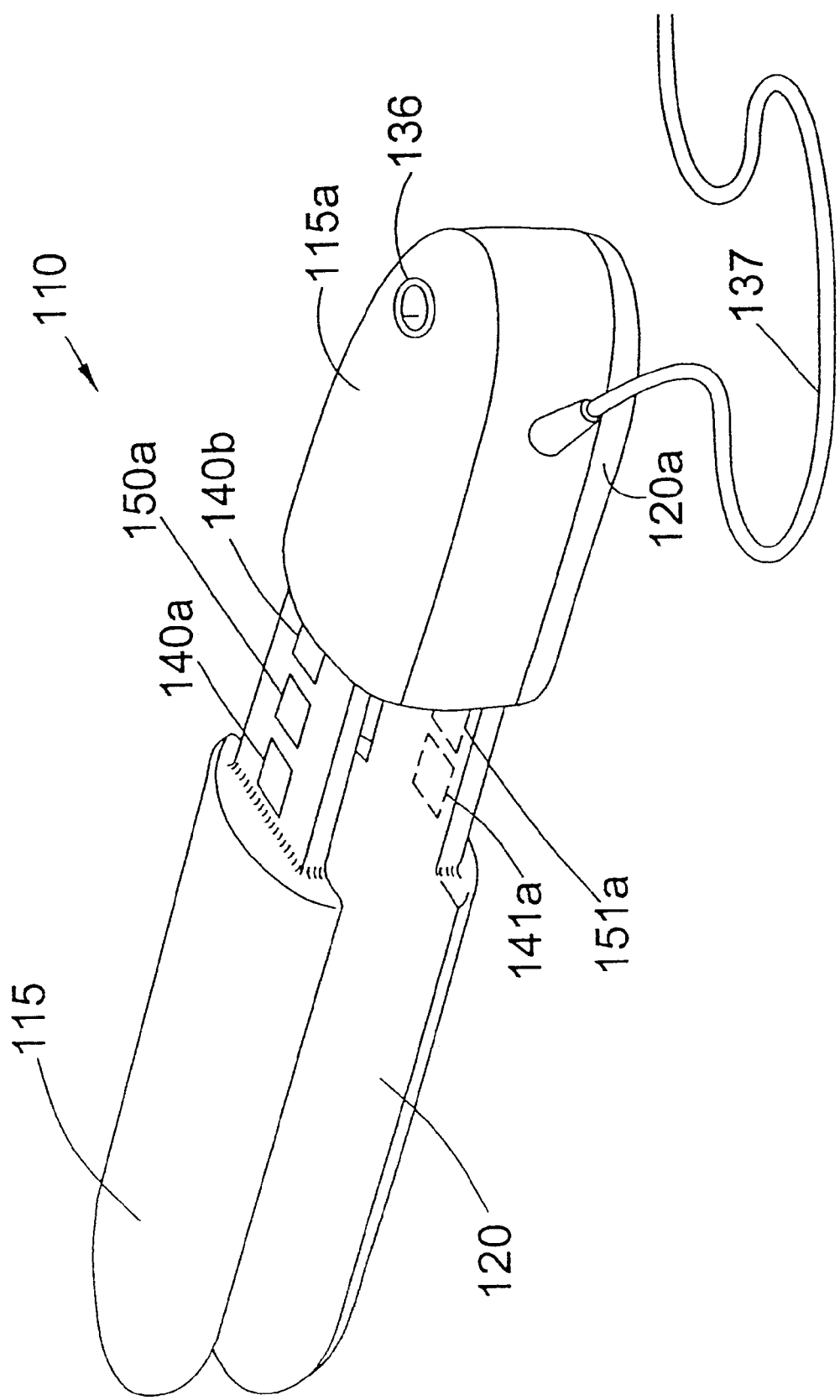
FIG. 2A is a perspective view of a second embodiment of an apparatus for measuring properties of the pelvic floor muscles according to the invention.
Figure 2B:
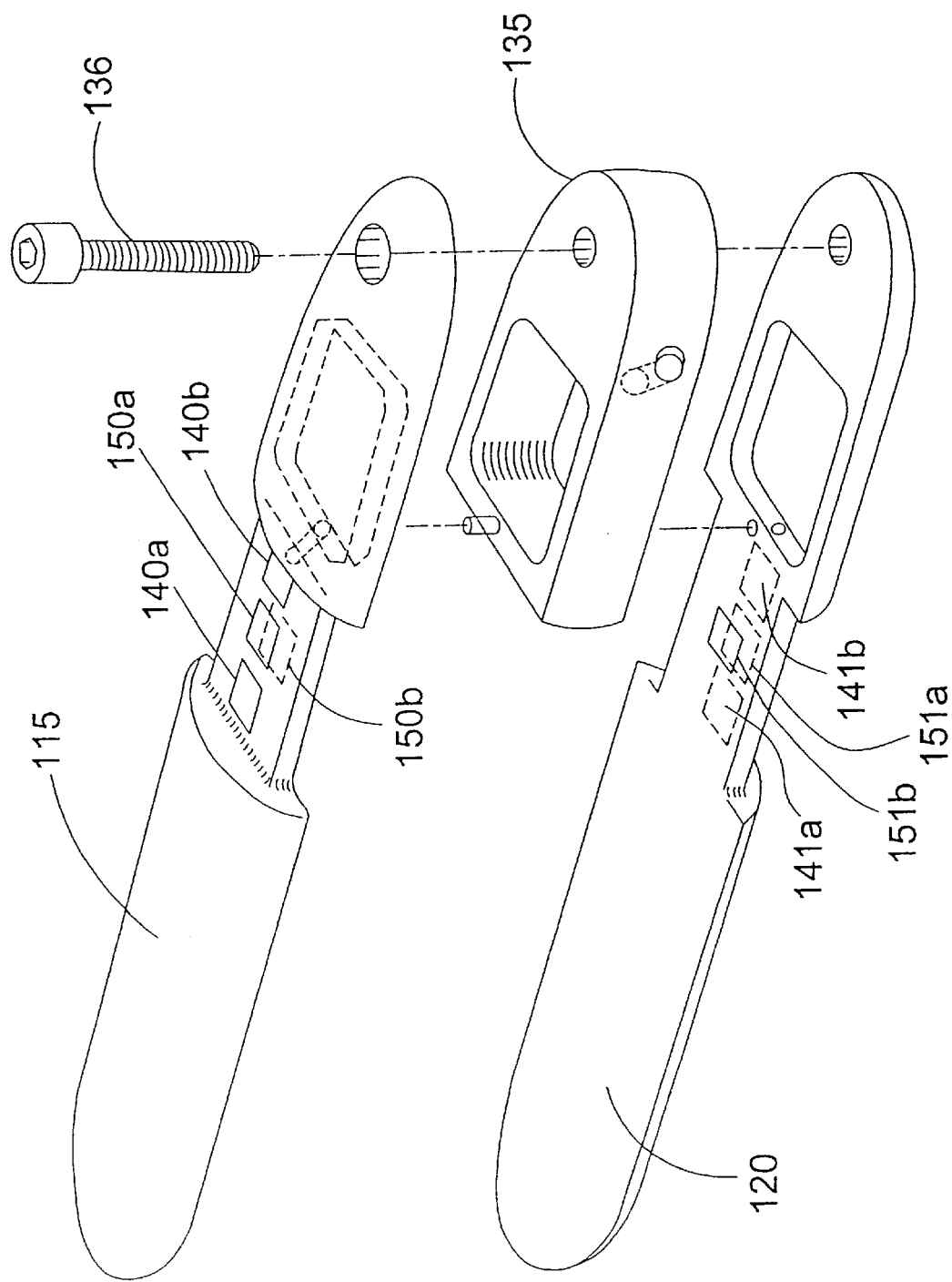
FIG. 2B is an expanded perspective view of the apparatus of FIG. 2A.

A second embodiment of an apparatus for measuring properties of the pelvic floor muscles according to the invention is shown in FIGS. 2A–2B. The apparatus 110 of FIGS. 2A–2B is similar to the apparatus 10 of FIG. 1A, and thus like references numerals have been utilized to refer to like elements. Further, repetitive explanation has been omitted.

In the embodiment of FIG. 2A, the two blades 115, 120 have similar-shaped end portions 115a, 120a. A spacer 135 is provided that holds the two blades 115a, 120a a predetermined distance apart, preferably within a range of approximately 0 to 10 cm. In tests it was found that blade separation distances, for example, of 5 mm, 2.0 and 4.5 cm were acceptable.

The spacer 135 may be hollow as shown in FIG. 2B to accommodate and protect gage wires, terminal blocks and/or preamplifiers. The spacer 135 also has a port 135a for receiving a lead wire 137, which, for example, leads signals to a recording device (not shown), display (not shown) and/or computer (not shown). As shown in FIG. 2B, a screw is preferably utilized to join elements 115a, 135 and 120a; however, other types of fasteners or means of joining the elements together are also permissible. When the blades 115, 120 and the spacer 135 are joined together, the blades are cantilevered and extend parallel and a fixed distance apart. Alternatively, the blades 115, 120 and the spacer 135 can be formed as a single unit.

The blades 115, 120, and spacers 135a are all preferably formed of a structural elastic material, such as anodized aluminum, stainless steel, titanium or a rigid structural material. The modulus of elasticity, cross-sectional geometry and overall geometric design are selected so as to yield sufficient microstrain in each gage section under full load, thereby yielding acceptable resolution of the smallest force that is clinically meaningful. The spacer thickness is selected such that under maximal loading, deflections of the blades will not result in adjacent blades touching one another.

A third embodiment of an apparatus for measuring properties of the pelvic floor muscles according to the invention is shown in FIGS. 3A–3C. This apparatus is intended for measuring pelvic floor strength. The apparatus of FIGS. 3A–3C is similar to the apparatus of FIGS. 1A–1C and 2A–2B and thus like references numerals have been used to represent like elements.

The apparatus 210 of FIGS. 3A–3C includes three elongated blades 215, 220, 225. The blades 215, 220, 225 are preferably shaped to facilitate insertion into, for example, the vagina or rectum. The blades are preferably approximately 2.5 cm in width; however, other widths may also be appropriate.

The blades 215, 220, 225 are preferably arranged substantially in parallel and and spaced at a predetermined fixed distance apart by spacers 235a, 235b, as shown in FIG. 3A. The spacers 235a, 235b may be fabricated as part of the blades, or may be separate pieces. The spacers are joined together with end portions of the blades by some type of fastening devices, for example, screws, snaps, a sliding connection, or adhesive. The other ends of the blades are then cantilevered extending out parallel to one another and a fixed distance apart.

The embodiment of FIGS. 3A–3C also includes a tissue blocking device 290 that prevents tissue from entering a gap between blades 220, 225. If tissue is allowed to enter the gap between blades 220, 225, it may affect the measurement, for example, by preventing deflection of the blades.

The tissue blocking device 290 includes a rod 295 that extends through a hole (shown in dashed line in FIGS. 3A–3B) in spacer 235b and between blades 220, 225. A discoid element 291 is rigidly connected to the rod 295. The dischoid element 291 prevents tissue from entering the gap between blades 220, 225 and affecting the measurement. Element 291 is shown as a disk in FIGS. 3A–3B; however, other shapes may also be appropriate. No prior art device has included such a tissue blocking device, and hence such devices are prone to artifacts.

Figure 3D:
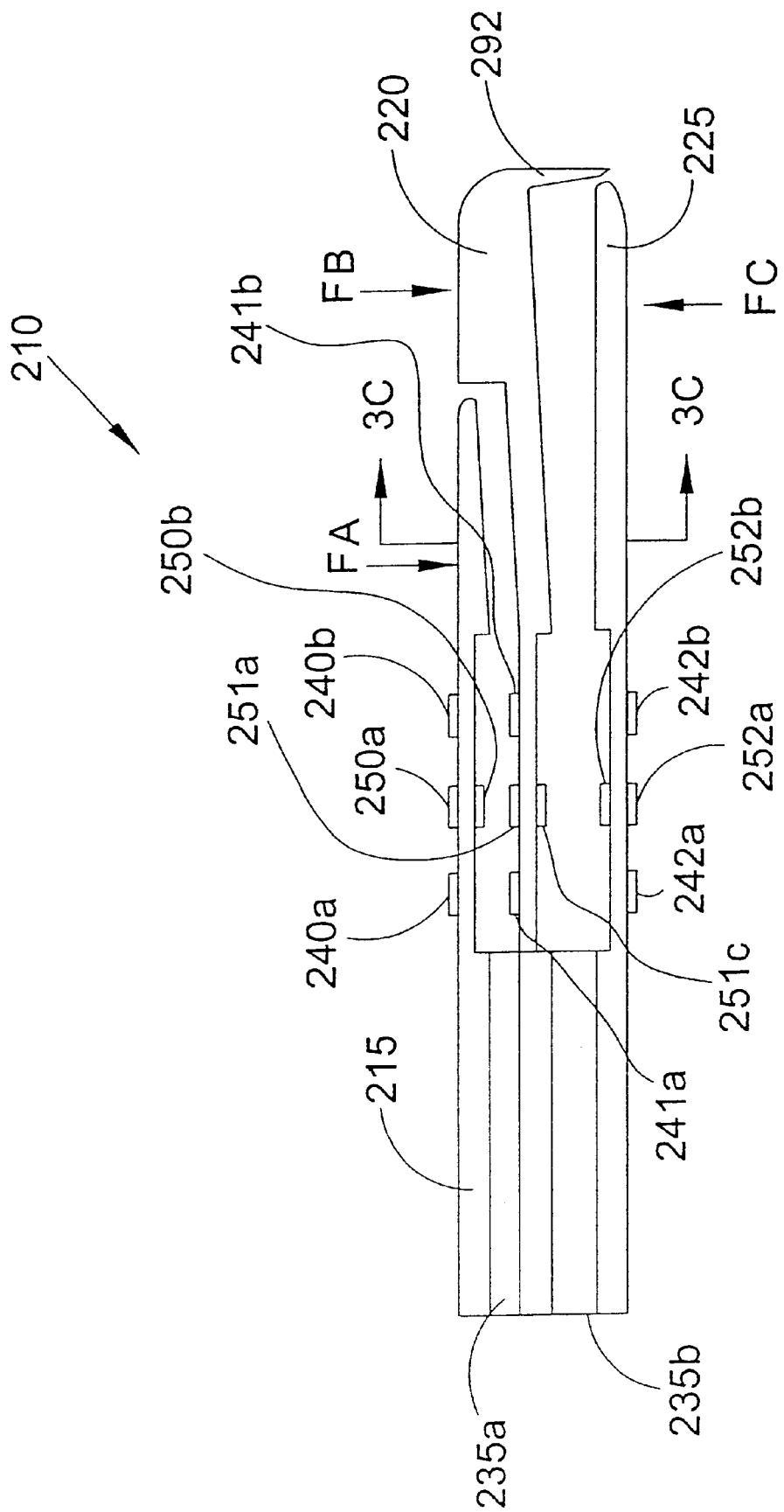
FIG. 3D is a side view of an alternative of the apparatus of FIG. 3A.

Alternatively, the lateral edges of the blades may be shaped so that a "skirt" 292 exists on the sides and/or the tips of the blades, as shown in FIG. 3D. This prevents tissue ingress between the blades. The skirt could be attached to one blade, as shown in FIG. 3D, or both blades in an overlapping arrangement (not shown).

The blades 215, 220, 225, spacers 235a, 235b and tissue blocking device 290 are all preferably formed of a structural elastic material, such as anodized aluminum, stainless steel, titanium or a rigid structural material. The modulus of elasticity, cross-sectional geometry and overall geometric design are selected so as to yield sufficient microstrain in each gage section under full load, thereby yielding acceptable resolution of the smallest force that is clinically meaningful. The spacer thickness is selected such that under maximal loading, deflections of the blades will not result in adjacent blades touching one another.

The first blade 215 includes, preferably within gage section 222, which may or may not be narrowed, strain gages 240a, 250a, 240b mounted on an upper surface of the blade, and strain gage 250b mounted on a lower surface of the blade, symmetrically with strain gage 250a. The second blade 220 includes, preferably within gage section 222, strain gages 241a, 251a, 241b mounted on an upper surface of the blade, and strain gage 251b mounted on a lower surface of the blade, symmetrically with strain gage 251a. The third blade 225 includes, preferably within gage section 222, strain gages 242a, 252a, 242b mounted on a lower surface of the blade, and strain gage 252 mounted on an upper surface of the blade, symmetrically with strain gage 252b.

The first blade 215 measures the reaction force $F_A$ developed by the pubic symphysis and intervening tissues. The second blade 220 measures the force $F_B$ due to the intraabdominal pressure. The third blade 225 measures the apparent force $F_C$ exerted by the pelvic floor muscles.

The measurement of shear force follows the description of a differential strain beam by P. C. Dechow et al. "A Method of Bite Force Measurements in Primates." J. Biomech., Vol. 16, No. 10, pp. 797–802, 1983, which is hereby incorporated by reference. The strain gage pairs 240a and 240b, 241a and 241b and 242a and 242b are each wired into separate Wheatstone bridge circuits so as to measure the shear force acting normal to each blade. A fixed voltage is applied to one set of opposite corners of the bridge, and the voltage drop across the other pair of opposite corners is amplified and displayed on any suitable display device or stored in digital form using an analog to digital converter. The output-of the device is calibrated by applying known static forces normal to each blade at known locations along the blade and noting the corresponding voltage changes. A calibration curve can then be constructed with one or more regression coefficients being found.

The strain gage pairs 251a and 251b, 251aand 251b, and 252a and 252b are wired to a Wheatstone bridge circuit so as to measure the bending moment applied to each blade. A fixed voltage is applied to one set of opposite corners of the bridge, and the voltage drop across the other pair of opposite corners is amplified and displayed on any suitable display device. The output of the device is calibrated by applying known static forces at known locations along the blade normal to each blade and noting the corresponding voltage changes. A calibration curve can then be constructed with one or more regression coefficients being found.

The method allows calculation of location of the resultant applied force on each blade. By dividing the calculated moment by the calculated shear force on that blade, the average calculated location along the blade at which the resultant force was applied to the each blade can be determined.

Figure 4C:
FIG. 4C is a cross-sectional view of the apparatus of FIG. 4A taken along line 4C—4C.
Figure 4A:
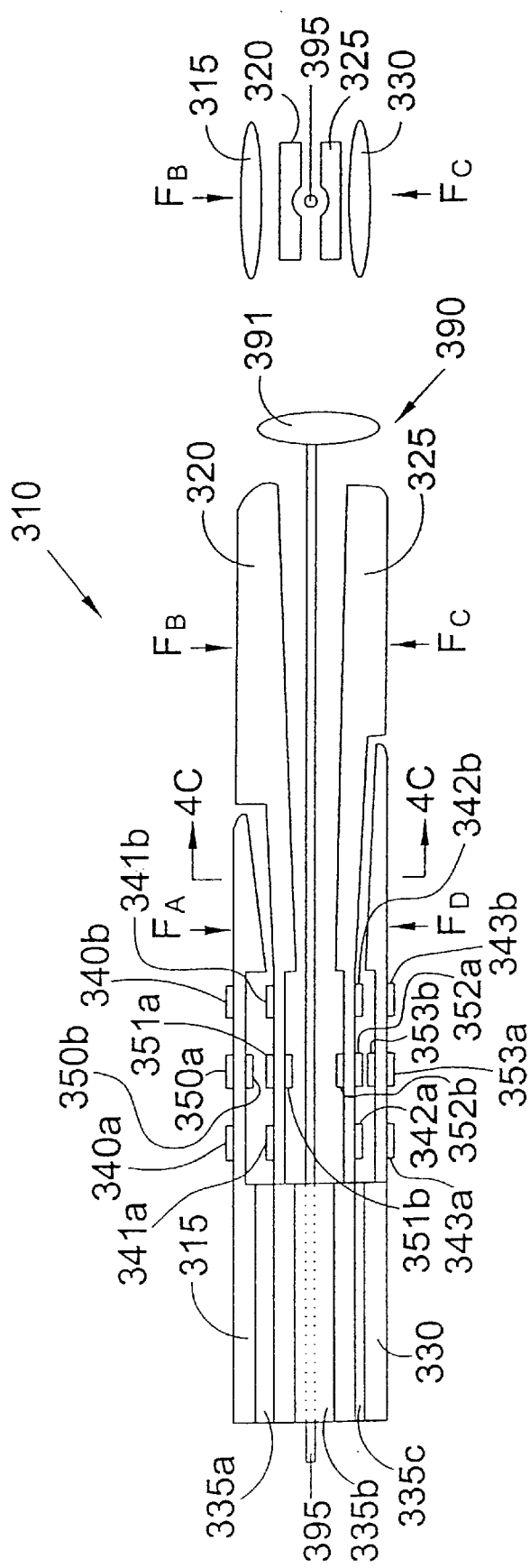
FIG. 4A is a side view of a fourth embodiment of an apparatus for measuring properties of the pelvic floor muscles according to the invention.
Figure 4B:
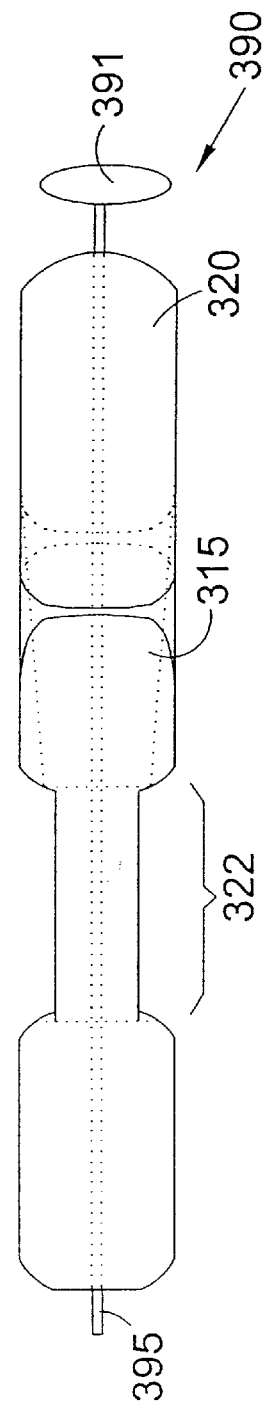
FIG. 4B is a top view of the apparatus of FIG. 4A.

A fourth embodiment of the invention is shown in FIGS. 4A–4C. The apparatus of FIGS. 4A–4C is similar to the apparatus of FIGS. 1, 2A–2B and 3A–3C and thus like reference numerals have been used to represent like elements. This apparatus is designed for measuring pelvic floor muscle strength in healthy women as well as those with prolapse.

The apparatus 310 of FIGS. 4A–4C includes four elongated blades 315, 320, 325, 330. The blades 315, 320, 325, 330 are preferably shaped to facilitate insertion into, for example, the vagina or rectum. The blades are preferably approximately 10 cm in width; however, other widths may also be appropriate.

The blades 315, 320, 325, 330 are preferably arranged substantially in parallel and spaced a predetermined distance apart by spacers 335a, 335b, 335c, as shown in FIG. 4A. The spacers 235a, 235b may be fabricated as part of the blades, or may be separate pieces. The spacers are joined together with ends of the blades by some type of fastening device, for example, screws, snaps, a sliding connection or adhesive. The other ends of the blades are then cantilevered extending out parallel to one another and a fixed distance apart.

The embodiment of FIGS. 4A–4C also includes a tissue blocking device 390 that prevents tissue from entering a gap between blades 320, 325. If tissue is allowed to enter the gap between blades 320, 325, it may affect the measurements, for example, by preventing deflection of the blades. The tissue blocking device 390 includes a rod 395 that extends through a hole (shown in dashed line in FIGS. 4A–4B) in spacer 335b and between blades 320, 325. A discoid element 391 is rigidly connected to the rod 395. The dischoid element 391 prevents tissue from entering the gap between blades 320, 325 and affecting the measurement. Element 391 is shown as a disk in FIGS. 4A–4B; however, other shapes may also be appropriate.

The blades 315, 320, 325, 330, spacers 335a, 335b, 335c, and tissue blocking device 390 are all preferably formed of a structural elastic material, such as anodized aluminum, stainless steel, titanium or a rigid structural material. The modulus of elasticity, cross-sectional geometry and overall geometric design of the blades are selected so as to yield sufficient microstrain in each gage section under full load, thereby yielding acceptable resolution of the smallest force that is clinically meaningful. The spacer thicknesses are selected such that under maximal loading, deflections of the blade will not result in adjacent blades touching one another.

The first blade 315 includes, preferably within gage section 322, which may or may not be narrowed, strain gages 340a, 350a, 340b mounted on an upper surface of the blade, and strain gage 350b mounted on a lower surface of the blade, symmetrically with strain gage 350a. The second blade 320 includes, preferably within gage section 322, strain gages 341a, 351a, 341b mounted on an upper surface of the blade, and strain gage 351b mounted on a lower surface of the blade, symmetrically with strain gage 351a. The third blade 325 includes, preferably within gage section 322, strain gages 342a, 352a, 342b mounted on a lower surface of the blades, and strain gage 352b mounted on an upper surface of the blade, symmetrically with strain gage 352a. The fourth blade 330 includes, preferably within the gage section 322, strain gages 343a, 353a, 343b mounted on a lower surface of the blade, and strain gage 353b mounted on an upper surface of the blade, symmetrically with strain gage 353a.

The first blade 315 measures the reaction force $F_A$ developed by the pubic symphysis and intervening tissues. The second blade 320 measures the force $F_B$ acting inferiorly on the apparatus. The third blade 325 measures the force $F_C$ exerted by IAP acting superiorly on the apparatus. The fourth blade 330 measures the apparent force $F_C$ exerted by the pelvic floor muscles.

The measurement of shear force again follows the description by Dechow et al. for the apparatus of FIGS. 4A–4C. The strain gage pairs 340a and 340b; 341a and 341b; 342a and 342b; and 343a and 343b are each wired into separate Wheatstone bridge circuits so as to measure the shear force acting normal to each blade. A fixed voltage is applied to one set of opposite corners of the bridge, and the voltage drop across the other pair of opposite corners is amplified and displayed on any suitable display device or stored in digital form using an analog to digital converter. The output of the device is calibrated by applying known static forces normal to each blade at known locations along the blade and noting the corresponding voltage changes. A calibration curve can then be constructed with one or more regression coefficients being found.

The strain gage pairs 350a and 350b; 351a and 351b; 352a and 352b and 353a and 353b are wired to a separate Wheatstone bridge circuits so as to measure the bending moment applied to each blade. A fixed voltage is applied to one set of opposite corners of the bridge, and the voltage drop across the other pair of opposite corners is amplified and displayed on any suitable display device. The output of the apparatus is calibrated by applying known static forces at known locations along the blade normal to each blade and noting the corresponding voltage changes. A calibration curve can then be constructed with one or more regression coefficients being found.

In women with a prolapse the prolapsing vagina everts under the action of increasing IAP, the center of the action of the force applied to blades 315, 320, 325 330 will tend to move proximately toward the blade tips. Hence, pelvic floor and IAP force measurements need to be made over a longer blade length than in intact women.

The method and apparatus according to the invention provide at least the following discussed advantages.

The substantially parallel blade relationship of the apparatus according to the invention allows any or all of the following standard physiological measurements of muscle contractility to be made under isometric conditions.

(a) maximum volitional pelvic floor muscle strength
(b) maximum pelvic floor muscle strength stimulated electrically
(c) maximum volitional rate of force development
(d) maximum endurance at a desired steady contraction intensity level
(e) maximum endurance time for repeated contractions of a set intensity and duration
(f) maximum rate of decreasing muscle force
(g) pelvic floor muscle force developed in a cough of known intraabdominal pressure
(h) pelvic floor muscle force developed in a valsalva maneuver
(i) pelvic floor muscle force developed during a lifting maneuver
(j) independent measurement of the effect of intraabdominal pressure acting during any or all of the above activities One of the standard physiological test conditions for testing the capacity of striated muscle to generate force is to measure that force development capacity while the muscle fibers are maintained at constant fiber length. This is because active striated muscle force development is known to be dependent upon muscle fiber length, due to the fact that the actin-myosin overlap can vary as a function of fiber length. Because the deflection of the elastic blade is negligible in relation to the length of the pelvic floor muscle fibers, their length does not change appreciably from resting to the fully activated state. Prior art devices consisting of compliant balloon designs all allow the muscle to shorten and so do not meet isometric test condition requirements. Hence, they do not allow isometric pelvic floor muscle properties to be gathered because, even if the volume of the balloon is fixed, the designs do not constrain the balloon diameter from being reduced while the balloon lengthens along the vagina under load.

Further, the prior art speculum designs have upper and lower blades with their handles hinged, not fixed as in the present design. The presence of the hinge does not guarantee an isometric test condition for the pelvic floor muscles because they may unintentionally be allowed to shorten as they contract.

The method and apparatus according to the invention correct for the confounding effect of a synergistic force rising from the action of intraabdominal (IAP) pressure on the exposed area of the blade. The confounding effect of this pressure in augmenting pelvic floor muscle force on the strength-measuring device has not been recognized previously. The proposed method and apparatus allow direct measurement of the IAP through the deformation of one or more blades, and then correction of the apparent pelvic floor muscle force by subtracting the force estimated to be due to the IAP from that due to the pelvic floor muscles. In prior art, in particular U.S. Pat. No. 4,971,036, the effect of an increase in IAP cannot be distinguished from the effect of a pelvic floor muscle contraction.

Essentially all women can increase IAP volitionally. However, as many as 10% of healthy intact women are unable to volitionally recruit their pelvic muscles to demonstrate their strength volitionally due to lack of motor control skill. The present invention permits identification of these women with impairments in pelvic floor muscle neuromuscular control. Moreover, in those women with bona fide impairments in muscle strength due to neurological impairment or fascial detachment, the present invention allow pelvic force to be evaluated independent of any intended or unintended changes in IAP. The apparatus according to the invention may be inserted into the vagina so that with one blade held against the symphysis pubis the other blade is allowed to solely measure IAP, unencumbered by the effect of any pelvic muscle contraction force, since no muscles are located in that region. Measurement of IAP with a bladed device is not a feature of the prior art.

The method and apparatus according to the invention allow measurement of the reaction force developed between the apparatus and the symphysis pubis and intervening tissues. This allows a check to be made of pelvic muscle force measurement validity, namely that the net force acting on the device is zero. When it is zero, the examiner is not applying static or dynamic forces that would bias the measurement of pelvic floor muscle force.

The method and apparatus according to the invention allow the isometric force developed by the pelvic floor muscles to be measured in a known direction because the blade direction is dependent on the spring constant of the speculum blades. By holding the device at a known angle against the symphysis pubis, the force developed by the pelvic floor muscles in a direction normal to the long axis of the substantially-parallel blades, in the plane of symmetry of the blade, is measured. Measurement of the force developed by the pelvic floor muscles in a prescribed direction or known direction is not a feature of the prior art.

The method and apparatus according to the invention permit calculation of location of the resultant applied force on each blade. By dividing the calculated moment by the calculated force, the average location at which the net force acting on the blade is located may be found at any point in time. The prior art does not allow such a measurement.

The method and apparatus according to the invention can be utilized to quantify the state of pelvic floor muscle strength. This is the only apparatus that has been developed for objectively and accurately quantifying the maximum volitional isometric strength of the pelvic floor muscles in healthy women, women with temporary neuromuscular damage following childbirth or other trauma, and women who have fascial detachments of the levator ani. It is suitable for use by nurses, physician assistants, physicians, physical therapists, obstetricians, gynecologists and urologists for use in evaluating pelvic floor function in cases with urinary and fecal incontinence, and recovery from child birth. Real-time measurements of isometric levator ani strength and endurance can conveniently be made in seconds in the supine lithotomy, side-lying (United Kingdom), or standing postures. In those women who are unable to volitionally contract intact levator ani, the apparatus and method can be used to measure the levator force developed during a deep cough instead, because our experience shows that it should be about 60% of the maximum voluntary strength. Further, the method and apparatus can be used for follow-up studies of many different types of fascial reattachment surgery for prolapse.

The method and apparatus according to the invention have been used in clinical tests to record maximal isometric voluntary levator ani force, maximum isometric voluntary levator ani force during a deep cough, maximal isometric voluntary levator force during a valsalva maneuver, maximum rate of developing isometric force during a quick contraction, and maximum endurance in several hundred women over the last few years. The average isometric levator ani strength of 62 women with average (SD) age 27.2 (5.5) years was found to be 11.8 (6.9)N. Test-retest repeatability of maximum voluntary strength was 13% from minute to minute and 27% from one week to the next.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. An apparatus for measuring properties of the pelvic floor muscles of a patient, comprising:
   two or more elongated blades disposed substantially parallel to one another a predetermined distance apart;
   one or more sensors that sense an amount of deflection of the first and second blades when the first and second blades are subjected to an external force; and
   a determining unit that determines properties of the pelvic floor muscles in response to an output of the one or more sensors.

2. The apparatus according to claim 1, wherein the two or more elongated blades comprise first and second elongated blades disposed substantially parallel to one another a predetermined distance apart.

3. The apparatus according to claim 2, wherein central longitudinal axes of the first and second blades extend substantially parallel a predetermined distance apart and wherein the predetermined distance is variable.

4. The apparatus according to claim 3, wherein the first and second blades have mating arms which allow them to be moved with respect to one another and a key adapted to lock the arms with respect to one another.

5. The apparatus according to claim 4, further comprising a graduated scale mounted on or engraved into at least one of said arms.

6. The apparatus according to claim 1, wherein the determining unit comprises at least one Wheatstone bridge circuit with which the one or more sensors electronically communicate.

7. The apparatus according to claim 2, wherein the one or more sensors comprises a plurality of strain gages disposed on the first and second blades.

8. The apparatus according to claim 7, wherein the plurality of strain gages comprise first, second and third strain gages mounted on an upper surface of the first blade and a fourth strain gage mounted on a lower surface of the first blade, symmetrically with the second strain gage, and fifth, sixth and seventh strain gages mounted on a lower surface of the second blade and an eighth stain gage mounted on an upper surface of the second blade, symmetrically with the sixth strain gage.

9. The apparatus according to claim 8, wherein an output of the first, third, fifth and seventh strain gages is utilized by the determining unit to determine a force to which the apparatus is subjected and the second, fourth, sixth and eighth stain gages are utilized by the determining unit to determine a moment to which the apparatus is subjected.

10. The apparatus according to claim 8, wherein the determining unit comprises first and second Wheatstone bridge circuits and wherein the first, third, fifth and seventh strain gages are connected to the first Wheatstone bridge circuit and the second, fourth, sixth and eighth stain gages are connected to the second Wheatstone bridge circuit.

11. The apparatus according to claim 8, wherein an output of the first Wheatstone bridge circuit is utilized to determine a force to which the apparatus is subjected and an output of the second Wheatstone bridge circuit is utilized to determine a moment to which the apparatus is subjected.

12. The apparatus according to claim 1, wherein the one or more sensors comprise one or more optical sensing devices.

13. The apparatus according to claim 1, wherein the determining unit determines a force to which the apparatus is subjected.

14. The apparatus according to claim 12, wherein the determining unit further determines a moment to which the apparatus is subjected.

15. The apparatus according to claim 2, further comprising a damping device disposed between the first and second blades.

16. The apparatus according to claim 15, wherein the determining unit determines a maximum strength of the pelvic floor muscles during a shortening contraction at a given velocity utilizing a predetermined force of resistance provided by the damping device.

17. The apparatus according to claim 2, further comprising an expansion device disposed between the first and second blades.

18. The apparatus according to claim 17, wherein the determining unit determines the pelvic floor muscle strength developed under a predetermined rate of muscle floor lengthening velocity utilizing a predetermined rate of expansion provided by the expansion device.

19. The apparatus according to claim 2, further comprising a third elongated blade disposed substantially parallel to the second blade, wherein one or more sensors sense an amount of deflection of the first, second and third blades when the first, second and third blades are subjected to an external force.

20. The apparatus according to claim 19, wherein the one or more sensors comprises a plurality of sensors mounted on each of the first, second and third blades.

21. The apparatus according to claim 20, wherein the determining unit determines a reaction force $F_A$ developed by the pubic symphysis and intervening tissues in response to the output of the plurality of sensors mounted on the first blade, a force $F_B$ due to intraabdominal pressure in response to the output of the plurality of sensors mounted on the second blade, and a force $F_C$ exerted by the pelvic floor muscles in response to the output of the plurality of sensors. mounted on the third blade.

22. The apparatus according to claim 2, further comprising a fourth elongated blade disposed adjacent to the third blade, wherein the plurality of sensors sense an amount of deflection of the first, second, third and fourth blades when the first, second, third and fourth blades are subjected to an external force.

23. The apparatus according to claim 22, wherein the one or more sensors comprise a plurality of sensors mounted on each of the first, second, third and fourth blades.

24. The apparatus according to claim 23, wherein the determining unit determines a reaction force $F_A$ developed by the pubic symphysis and intervening tissues in response to the output of the plurality of sensors mounted on the first blade, a force $F_B$ acting inferiorly on the apparatus in response to the output of the plurality of sensors mounted on the second blade, a force $F_C$ acting superiorly on the apparatus in response to the output of the plurality of sensors mounted on the third blade, and a force $F_D$ exerted by the pelvic floor muscles in response to the output of the plurality of sensors mounted on the fourth blade.

25. The apparatus according to claim 22, further comprising at least three spacers, a first of the at least three spacers being disposed between the first and second blades, a second of the at least three spacers being disposed between the second and third blades and a third of the at least three spacers being disposed between the third and fourth blades, the at least three spacers maintaining the first and second blades, second and third blades and the third and fourth, respectively, at a fixed distance apart.

26. The apparatus according to claim 2, wherein the one or more sensors are mounted on narrowed portions of said first and second blades.

27. The apparatus according to claim 2, wherein the one or more sensors comprise a plurality of strain gages mounted on narrowed portions of said first and second blades.

28. The apparatus according to claim 1, further comprising a display in communication with the one or more sensors.

29. The apparatus according to claim 1, further comprising a computer in communication with the one or more sensors.

30. The apparatus according to claim 1, wherein ends of the blades are constrained in a fixed geometric relationship to each other so as to act as cantilevers.

31. An apparatus for measuring properties of the pelvic floor muscles of a patient, comprising:

two or more elongated blades disposed adjacent to one another;

one or more sensors that sense an amount of deflection of the first and second blades when the first and second blades are subjected to an external force; and a determining unit that determines properties of the pelvic floor muscles in response to an output of the one or more sensors; and wherein central longitudinal axes of the first and second blades extend substantially in parallel a predetermined distance apart wherein the predetermined distance is fixed.

32. The apparatus according to claim 31, further comprising a spacer positioned between the first and second blades that holds the first and second blades the fixed distance apart.

33. The apparatus according to claim 32, wherein the first and second blades and the spacer are integrally formed.

34. The apparatus according to claim 32, wherein the spacer is a separate piece and the first and second blades and the spacer are joined by a fastener.

35. An apparatus for measuring properties of the pelvic floor muscles of a patient, comprising:

first and second elongated blades disposed adjacent to one another;

one or more sensors that sense an amount of deflection of the first and second blades when the first and second blades are subjected to an external force; and a determining unit that determines properties of the pelvic floor muscles in response to an output of the one or more sensors; and a tissue blocking device that prevents a patient's tissue from entering a gap between the first and second blades.

36. The apparatus according to claim 35, wherein the tissue blocking device comprises a skirt that extends from at least one of the first and second blades.

37. The apparatus according to claim 35, wherein the tissue blocking device comprises a rod that extends between the first and second blades and a blocking element rigidly affixed thereto.

38. An apparatus for measuring properties of the pelvic floor muscles of a patient, comprising:

first and second elongated blades disposed adjacent to one another;

one or more sensors that sense an amount of deflection of the first and second blades when the first and second blades are subjected to an external force; and a determining unit that determines properties of the pelvic floor muscles in response to an output of the one or more sensors a third elongated blade disposed adjacent to the second blade, wherein one or more sensors sense an amount of deflection of the first, second and third blades when the first, second and third blades are subjected to an external force; and at least two spacers, one of the at least two spacers being disposed between the first and second blades and the other of the at least two spacers being disposed between the second and third blades, the at least two spacers maintaining the first and second blades and second and third blades, respectively, at a fixed distance apart.

39. An apparatus for measuring properties of the pelvic floor muscles of a patient, comprising:

a first elongated blade;

a second elongated blade disposed at a predetermined distance apart and extending substantially in parallel with the first blade; and one or more sensors that sense an amount of deflection of the first and second blades when subjected to an external force.

40. The apparatus according to claim 39, wherein the predetermined distance is fixed.

41. The apparatus according to claim 39, further comprising a spacer positioned between the first and second blades that holds the first and second blades the fixed distance apart.

42. The device according the claim 41, wherein the first and second blades and the spacer are integrally formed.

43. The apparatus according to claim 39, wherein the predetermined distance is variable.

44. The apparatus according to claim 43, wherein the first and second blades have mating arms which allow them to be moved with respect to one another to vary the predetermined distance and a key adapted to lock the arms with respect to one another.

45. The apparatus according to claim 41, further comprising a graduated scale mounted on or engraved into at least one of the arms.

46. The device according to claim 39, wherein the one or more sensors comprise a plurality of strain gages mounted on the first and second blades.

47. The device according to claim 39, wherein the one or more sensors comprise one or more optical sensing devices.

48. An apparatus for measuring properties of the pelvic floor muscles of a patient, comprising:

a first elongated blade;

a second elongated blade disposed adjacent to the first blade;

one or more sensors that sense an amount of deflection of the first and second blades when subjected to an external force; and a tissue blocking device that prevents a patient's tissue from entering a gap between the first and second blades.

49. The apparatus according to claim 48, wherein the tissue blocking device comprises a skirt that extends from at least one of the first and second blades.

50. The apparatus according to claim 49, wherein the tissue blocking device comprises a rod that extends between the first and second blades and a blocking element rigidly affixed thereto.

51. An apparatus for measuring properties of the pelvic floor muscles of a patient, comprising:

two or more elongated blades disposed adjacent to one another;

one or more sensors that sense an amount of deflection of the first and second blades when the first and second blades are subjected to an external force; and a determining unit that determines properties of the pelvic floor muscles in response to an output of the one or more sensors wherein the one or more sensors comprise a piezoelectric or piezoresistive film disposed on the one or more blades.

52. A method for measuring properties of the pelvic floor muscles of a patient, comprising:

inserting one or more elongated blades into the vagina or rectum of a patient;

determining a force acting on the one or more blades; and determining a moment acting on the one or more blades.

53. The method according to claim 52, further comprising determining an intraabdominal pressure exerted on the one or more elongated blades.

54. The method according to claim 52, further comprising subtracting the intraabdominal pressure from the force acting on the one or more blades.

55. The method according to claim 52, wherein the one or more elongated blades comprise first and second elongated blades, central longitudinal axes of the first and second elongated blades extending substantially in parallel at a predetermined distance apart.

56. The method according to claim 52, wherein each of the first and second blades has a plurality of sensors mounted thereon and the steps of determining a force acting on the one or more blades and determining a moment acting on the one or more blades comprises utilizing the output of the plurality of sensors to determine a force and a moment acting on the first and second blades.

57. The method according to claim 56, wherein the plurality of sensors comprise a plurality of strain gages.

58. The method according to claim 52, wherein the one or more elongated blades comprise first, second and third elongated blades, central longitudinal axes of the first, second and third elongated blades extending substantially in parallel at a predetermined distance apart.

59. The method according to claim 58, wherein each of the first, second and third blades has a plurality of sensors mounted thereon and the step of determining a force acting on the one or more blades comprises determining a reaction force $F_A$ developed by the pubic symphysis and intervening tissues in response to an output of the plurality of sensors mounted on the first blade, a force $F_B$ due to intraabdominal pressure in response to an output of the plurality of sensors mounted on the second blade, and a force $F_C$ exerted by the pelvic floor muscles in response to an output of the plurality of sensors mounted on the third blade.

60. The method according to claim 59, wherein the plurality of sensors comprise a plurality of strain gages.

61. The method according to claim 52, wherein the one or more elongated blades comprise first, second, third and fourth elongated blades, central longitudinal axes of the first, second, third and fourth elongated blades extending substantially in parallel at a predetermined distance apart.

62. The method according to claim 61, wherein each of the first, second and third blades has a plurality of sensors mounted thereon and the step of determining a force acting on the one or more blades comprises determining a reaction force $F_A$ developed by the pubic symphysis and intervening tissues in response to the output of the plurality of sensors mounted on the first blade, a force $F_B$ acting inferiorly on the apparatus in response to the output of the plurality of sensors mounted on the second blade, a force $F_C$ acting superiorly on the apparatus in response to the output of the plurality of sensors mounted on the third blade, and a force $F_D$ exerted by the pelvic floor muscles in response to the output of the plurality of sensors mounted on the fourth blade.

63. A method for measuring properties of the pelvic floor muscles of a patient, comprising:

inserting one or more elongated blades into the vagina or rectum of a patient;

determining a force acting on the one or more blades;

determining an intraabdominal pressure exerted on the one or more elongated blades; and subtracting the intraabdominal pressure from the force acting on the one or more blades.

64. A method for measuring properties of the pelvic floor muscles of a patient, comprising:

inserting at least two elongated blades into the vagina or rectum of a patient, the at least two elongated blades having a damping device disposed therebetween; and determining a force acting on the one or more blades utilizing the known resistance provided by the damping device.

65. A method for measuring properties of the pelvic floor muscles of a patient, comprising:

inserting at least two elongated blades into the vagina or rectum of a patient, the at least two elongated blades having a expansion device disposed therebetween; and determining a force acting on the one or more blades utilizing the known expansion rate provided by the expansion device.

66. An apparatus for measuring properties of pelvic floor muscles of a subject, comprising:

at least two extension units extending substantially parallel to one another, each including a plurality of sensors that output a plurality of sensor signals; and a determining unit for receiving the plurality of sensor signals and configured to determine data from the plurality of sensor signals relevant to the pelvic floor muscles of a subject.

67. The apparatus according to claim 66, wherein the determining unit comprises passive elements.

68. The apparatus according to claim 66, wherein the plurality of sensors comprises a plurality of stress sensors.

69. The apparatus according to claim 66, wherein the determining unit decouples the force and moment information from the plurality of sensor signals.

70. The apparatus according to claim 66, wherein the determining unit is coupled to a processor.

71. The apparatus according to claim 70, wherein external information is combined with the data by the processor.

72. The apparatus according to claim 71, wherein the external information comprises image information.

73. An apparatus for measuring properties of the pelvic floor muscles of a patient, comprising;

two or more elongated blades disposed adjacent to one another;

one or more sensors that sense an amount of deflection of the first and second blades when the first and second blades are subjected to an external force; and a determining unit that determines properties of the pelvic floor muscles in response to an output of the one or more sensors, wherein the one or more sensors comprises a plurality of strain gages disposed on the first and second blades and wherein the plurality of strain gages comprise first, second and third strain gages mounted on an upper surface of the first blade and a fourth strain gage mounted on a lower surface of the first blade, symmetrically with the second strain gage, and fifth, sixth and seventh strain gages mounted on a lower surface of the second blade and an eighth stain gage mounted on an upper surface of the second blade, symmetrically with the sixth strain gage.

74. The apparatus according to claim 73, wherein an output of the first, third, fifth and seventh strain gages is utilized by the determining unit to determine a force to which the apparatus is subjected and the second, fourth, sixth and eighth stain gages are utilized by the determining unit to determine a moment to which the apparatus is subjected.

75. The apparatus according to claim 73, wherein the determining unit comprises first and second Wheatstone bridge circuits and wherein the first, third, fifth and seventh strain gages are connected to the first Wheatstone bridge circuit and the second, fourth, sixth and eighth stain gages are connected to the second Wheatstone bridge circuit.

76. The apparatus according to claim 75, wherein an output of the first Wheatstone bridge circuit is utilized to determine a force to which the apparatus is subjected and an output of the second Wheatstone bridge circuit is utilized to determine a moment to which the apparatus is subjected.

77. An apparatus for measuring properties of the pelvic floor muscles of a patient, comprising:

first, second, third and fourth elongated blades disposed adjacent to one another;

one or more sensors that sense an amount of deflection of the first, second, third and fourth blades when the first, second, third and fourth blades are subjected to an external force; and a determining unit that determines properties of the pelvic floor muscles in response to an output of the one or more sensors.

78. The apparatus according to claim 77, wherein the one or more sensors comprise a plurality of sensors mounted on each of the first, second, third and fourth blades.

79. The apparatus according to claim 78, wherein the determining unit determines a reaction force $F_A$ developed by the pubic symphysis and intervening tissues in response to the output of the plurality of sensors mounted on the first blade, a force $F_B$ acting inferiorly on the apparatus in response to the output of the plurality of sensors mounted on the second blade, a force $F_C$ acting superiorly on the apparatus in response to the output of the plurality of sensors mounted on the third blade, and a force $F_D$ exerted by the pelvic floor muscles in response to the output of the plurality of sensors mounted on the fourth blade.

80. The apparatus according to claim 77, further comprising at least three spacers, a first of the at least three spacers being disposed between the first and second blades, a second of the at least three spacers being disposed between the second and third blades and a third of the at least three spacers being disposed between the third and fourth blades, the at least three spacers maintaining the first and second blades, second and third blades and the third and fourth, respectively, at a fixed distance apart.

81. An apparatus for measuring properties of the pelvic floor muscles of a patient, comprising:

two or more elongated blades disposed adjacent to one another;

one or more sensors that sense an amount of deflection of the two or more blades when the two or more blades are subjected to an external force; and a determining unit that determines properties of the pelvic floor muscles in response to an output of the one or more sensors, wherein ends of the blades are constrained in a fixed geometric relationship to each other so as to act as cantilevers.

82. An apparatus for measuring properties of the pelvic floor muscles of a patient, comprising:

two or more elongated blades disposed adjacent to one another;

a plurality of sensors that sense an amount of deflection of the first and second blades when the first and second blades are subjected to an external force; and a determining unit that determines a force to which the apparatus is subjected in response to an output of the plurality of sensors by determining an average stress over a length of each of the one or more elongated blades and estimating the force to which the apparatus is subjected.

83. The apparatus according to claim 82, wherein the plurality of sensors comprise at least one pair of strain gages.

84. An apparatus for measuring properties of the pelvic floor muscles of a patient, comprising:

two or more elongated blades disposed adjacent to one another;

one or more sensors that sense an amount of deflection of the blades when the two or more blades are subjected to an external force;

a determining unit that determines properties of the pelvic floor muscles in response to an output of the one or more sensors; and a handle rigidly attached to the two or more elongated blades.

* * * * *